United States Patent
Thomas et al.

(10) Patent No.: US 10,494,424 B2
(45) Date of Patent: Dec. 3, 2019

(54) METHODS AND COMPOSITIONS FOR THE TREATMENT OF DISEASES AND DISORDERS

(71) Applicant: LANKENAU INSTITUTE FOR MEDICAL RESEARCH, Wynnewood, PA (US)

(72) Inventors: Sunil Thomas, Philadelphia, PA (US); James Mullin, Havertown, PA (US); George C. Prendergast, Penn Valley, PA (US)

(73) Assignee: LANKENAU INSTITUTE FOR MEDICAL RESEARCH, Wynnewood, PA (US)

( * ) Notice: Subject to any disclaimer, the term of this patent is extended or adjusted under 35 U.S.C. 154(b) by 0 days.

(21) Appl. No.: 15/544,917

(22) PCT Filed: Jan. 20, 2016

(86) PCT No.: PCT/US2016/014030
§ 371 (c)(1),
(2) Date: Jul. 20, 2017

(87) PCT Pub. No.: WO2016/118568
PCT Pub. Date: Jul. 28, 2016

(65) Prior Publication Data
US 2018/0009882 A1     Jan. 11, 2018

Related U.S. Application Data

(60) Provisional application No. 62/105,358, filed on Jan. 20, 2015.

(51) Int. Cl.
| | | |
|---|---|---|
| *C07K 16/18* | (2006.01) | |
| *A61K 39/395* | (2006.01) | |
| *A61K 45/06* | (2006.01) | |
| *A61K 39/00* | (2006.01) | |
| *A61P 37/00* | (2006.01) | |

(52) U.S. Cl.
CPC .......... *C07K 16/18* (2013.01); *A61K 39/3955* (2013.01); *A61K 45/06* (2013.01); *A61K 2039/505* (2013.01); *A61P 37/00* (2018.01); *C07K 2317/34* (2013.01)

(58) Field of Classification Search
CPC ............... C07K 16/18; C07K 2317/34; C07K 2317/76; A61K 39/3955; A61K 2039/505; A61K 45/06; A61P 29/00; A61P 37/06
See application file for complete search history.

(56) References Cited

U.S. PATENT DOCUMENTS

| 6,048,702 A | 4/2000 | Prendergast et al. | |
| 2003/0166021 A1* | 9/2003 | Prendergast | ....... C07K 14/4702 |
| | | | 435/7.23 |
| 2006/0177444 A1* | 8/2006 | Horizoe | ................. A61K 31/00 |
| | | | 424/145.1 |
| 2014/0044718 A1 | 2/2014 | McKenzie et al. | |
| 2014/0302502 A1 | 10/2014 | Shaw et al. | |

FOREIGN PATENT DOCUMENTS

WO     1998/055151 A1     12/1998

OTHER PUBLICATIONS

Tan, M.S., et al., "Bridging integrator 1 (BIN1): form, function, and Alzheimer's disease" Trends Mol. Med. (2013) 19 (10):594-603.
Chang, M.Y., et al., "Bin1 Attenuation Suppresses Experimental Colitis by Enforcing Intestinal Barrier Function" Dig. Dis. Sci. (2012) 57:1813-1821.
Duhadaway, J.B., et al., "Immunohistochemical Analysis of Bin1/Amphiphysin II in Human Tissues: Diverse Sites of Nuclear Expression and Losses in Prostate Cancer" J. Cell. Biochem. (2003) 88:635-642.
Wechsler-Reya, R., et al., "The Putative Tumor Suppressor BIN1 is a Short-Lived Nuclear Phosphoprotein, the Localization of Which is Altered in Malignant Cells" Cancer Res. (1997) 57(15):3258-63.
Prendergast, G.C., et al., "BAR the door: cancer suppression by amphiphysin-like genes" Biochim. Biophys. Acta. (2009) 1795(1):25-36.
Muller, A.J., et al., "Marrying immunotherapy with chemotherapy: why say IDO?" Cancer Res. (2005) 65 (18):8065-8068.
Seshadri, S., et al., "Genome-wide analysis of genetic loci associated with Alzheimer disease" JAMA (2010) 303 (18)1832-40.
Hu, X., et al., "Meta-Analysis for Genome-Wide Association Study Identities Multiple Variants at the BIN1 Locus Associated with Late-Onset Alzheimer's Disease" PLoS One (2011) 6(2):e16616.
Karch, C.M., et al., "Expression of Novel Alzheimer's Disease Risk Genes in Control and Alzheimer's Disease Brains" PLoS One (2012) 7(11):e50976.
Chapuis, J., et al., "Increased expression of BIN1 mediates Alzheimer genetic risk by modulating tau pathology" Mol. Psychiatry (2013) 18(11):1225-34.
Holler, C.J., et al., "Bridging Integrator 1 (BIN1) Protein Expression Increases in the Alzheimer's Disease Brain and Correlates with Neurofibrillary Tangle Pathology" J. Alzheimers Dis. (2014) 42(4):1221-1227.
Ryu, H., et al., "Bin1: a new player in IBD barrier dysfunction" Dig. Dis. Sci. (2012) 57(7):1751-3.
Chang. M.Y., et al., "BIN1 (bridging integrator 1)" Atlas Genet. Cytogenet. Oncol. Haematol. (2009) 13(8):543-548.
Thomas, S., et al., "Novel Colitis Immunotherapy Targets Bin1 and Improves Colon Cell Barrier Function" Dig. Dis. Sci. (2016) 61(2):423-32.

* cited by examiner

*Primary Examiner* — Kimberly Ballard
(74) *Attorney, Agent, or Firm* — Robert C. Netter, Jr.; Dann, Dorfman, Herrell & Skillman

(57) ABSTRACT

Compositions and methods for the treatment of a disease or disorder are disclosed.

6 Claims, 12 Drawing Sheets
Specification includes a Sequence Listing.

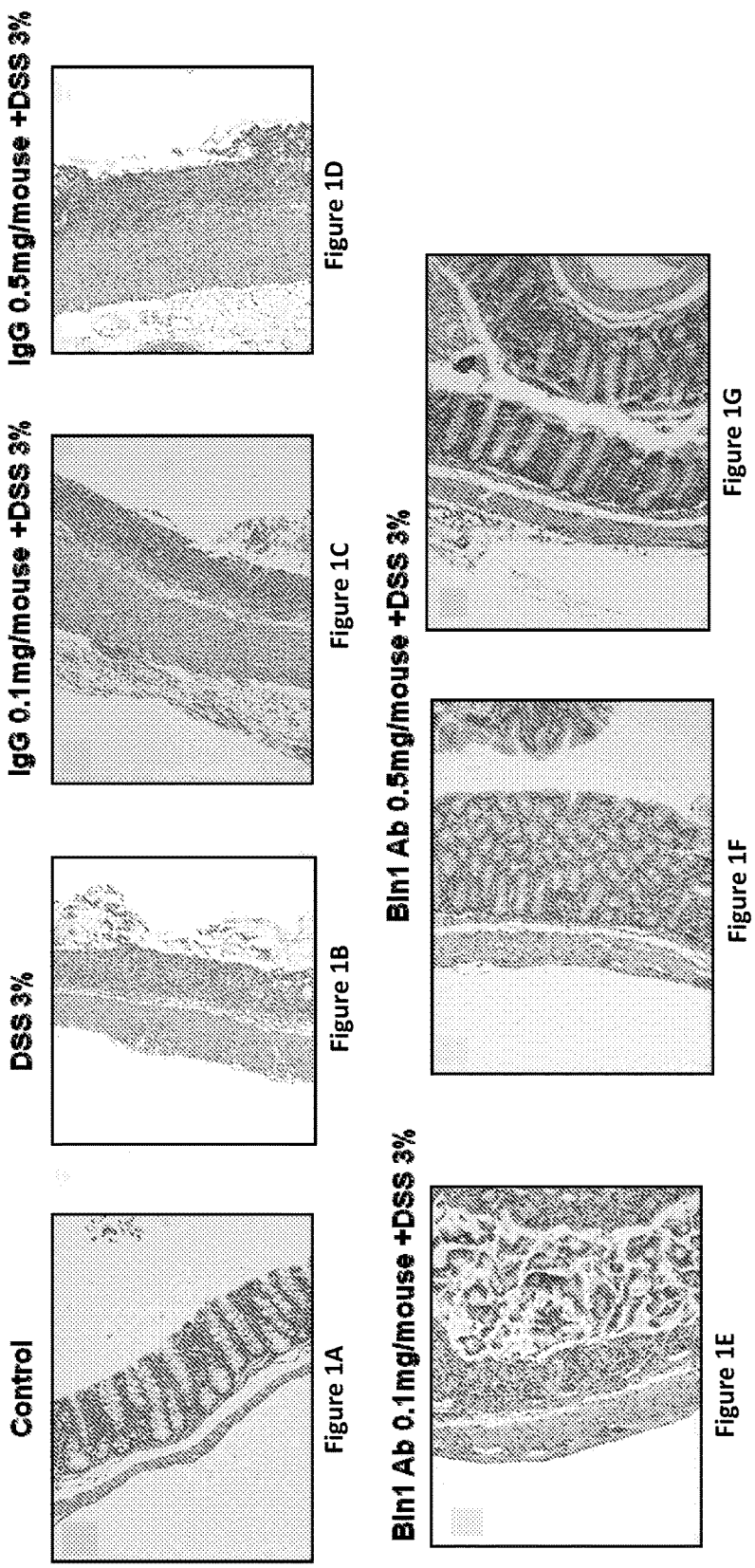

```
                          SEQUENCE LISTING

<160> NUMBER OF SEQ ID NOS: 2

<210> SEQ ID NO 1
<211> LENGTH: 451
<212> TYPE: PRT
<213> ORGANISM: Homo sapiens

<400> SEQUENCE: 1

Met Leu Trp Asn Val Val Thr Ala Gly Lys Ile Ala Ser Asn Val Gln
1               5                   10                  15

Lys Lys Leu Thr Arg Ala Gln Glu Lys Val Leu Gln Lys Leu Gly Lys
            20                  25                  30

Ala Asp Glu Thr Lys Asp Glu Gln Phe Glu Gln Cys Val Gln Asn Phe
        35                  40                  45

Asn Lys Gln Leu Thr Glu Gly Thr Arg Leu Gln Lys Asp Leu Arg Thr
    50                  55                  60

Tyr Leu Ala Ser Val Lys Ala Met His Glu Ala Ser Lys Lys Leu Asn
65                  70                  75                  80

Glu Cys Leu Gln Glu Val Tyr Glu Pro Asp Trp Pro Gly Arg Asp Glu
                85                  90                  95

Ala Asn Lys Ile Ala Glu Asn Asn Asp Leu Leu Trp Met Asp Tyr His
            100                 105                 110

Gln Lys Leu Val Asp Gln Ala Leu Leu Thr Met Asp Thr Tyr Leu Gly
        115                 120                 125

Gln Phe Pro Asp Ile Lys Ser Arg Ile Ala Lys Arg Gly Arg Lys Leu
    130                 135                 140

Val Asp Tyr Asp Ser Ala Arg His His Tyr Glu Ser Leu Gln Thr Ala
145                 150                 155                 160

Lys Lys Lys Asp Glu Ala Lys Ile Ala Lys Ala Glu Glu Glu Leu Ile
                165                 170                 175

Lys Ala Gln Lys Val Phe Glu Glu Met Asn Val Asp Leu Gln Glu Glu
            180                 185                 190

Leu Pro Ser Leu Trp Asn Ser Arg Val Gly Phe Tyr Val Asn Thr Phe
        195                 200                 205

Gln Ser Ile Ala Gly Leu Glu Glu Asn Phe His Lys Glu Met Ser Lys
    210                 215                 220

Leu Asn Gln Asn Leu Asn Asp Val Leu Val Gly Leu Glu Lys Gln His
225                 230                 235                 240

Gly Ser Asn Thr Phe Thr Val Lys Ala Gln Pro Arg Lys Lys Ser Lys
                245                 250                 255

Leu Phe Ser Arg Leu Arg Arg Lys Lys Asn Ser Asp Asn Ala Pro Ala
            260                 265                 270

Lys Gly Asn Lys Ser Pro Ser Pro Asp Gly Ser Pro Ala Ala Thr
        275                 280                 285

Pro Glu Ile Arg Val Asn His Glu Pro Glu Pro Ala Gly Gly Ala Thr
    290                 295                 300

Pro Gly Ala Thr Leu Pro Lys Ser Pro Ser Gln Pro Ala Glu Ala Ser
305                 310                 315                 320

Glu Val Ala Gly Gly Thr Gln Pro Ala Ala Gly Ala Gln Glu Pro Gly
                325                 330                 335
```

```
Glu Thr Ala Ala Ser Glu Ala Ala Ser Ser Leu Pro Ala Val Val
            340                 345                 350

Val Glu Thr Phe Pro Ala Thr Val Asn Gly Thr Val Glu Gly Gly Ser
        355                 360                 365

Gly Ala Gly Arg Leu Asp Leu Pro Pro Gly Phe Met Phe Lys Val Gln
        370                 375                 380

Ala Gln His Asp Tyr Thr Ala Thr Asp Thr Asp Glu Leu Gln Leu Lys
385                 390                 395                 400

Ala Gly Asp Val Val Leu Val Ile Pro Phe Gln Asn Pro Glu Glu Gln
                405                 410                 415

Asp Glu Gly Trp Leu Met Gly Val Lys Glu Ser Asp Trp Asn Gln His
                420                 425                 430

Lys Lys Leu Glu Lys Cys Arg Gly Val Phe Pro Glu Asn Phe Thr Glu
        435                 440                 445

Arg Val Pro
    450

<210> SEQ ID NO 2
<211> LENGTH: 34
<212> TYPE: PRT
<213> ORGANISM: Artificial Sequence
<220> FEATURE:
<223> OTHER INFORMATION: Bin1 fragment

<400> SEQUENCE: 2

Ala Gly Gly Thr Gln Pro Ala Ala Gly Ala Gln Glu Pro Gly Glu Thr
1               5                   10                  15

Ala Ala Ser Glu Ala Ala Ser Ser Ser Leu Pro Ala Val Val Val Glu
                20                  25                  30

Thr Phe
```

METHODS AND COMPOSITIONS FOR THE TREATMENT OF DISEASES AND DISORDERS

This application is a § 371 application of PCT/US2016/014030, filed Jan. 20, 2016, which claims priority under 35 U.S.C. § 119(e) to U.S. Provisional Patent Application No. 62/105,358, filed on Jan. 20, 2015. The foregoing applications are incorporated by reference herein.

FIELD OF THE INVENTION

This invention relates generally to the field of immunotherapy. Specifically, the invention provides novel compositions and methods for the treatment of diseases and disorders by administration of anti-Bin1 antibodies.

BACKGROUND OF THE INVENTION

Ulcerative colitis (UC) is a form of inflammatory bowel disease (IBD) associated with the large intestine (colon) and its frequency in developed countries has been increasing since the mid 20th century (Danese et al. (2011) N. Engl. J. Med., 365:1713-25). The highest incidence and prevalence of IBD is seen in the populations of Northern Europe and North America and the lowest in Asia. A Westernized environment and lifestyle is linked to the appearance of IBD, which is associated with smoking, diets high in fat and sugar, medication use, stress, and high socioeconomic status. The incidence of UC is 1.2 to 20.3 cases per 100,000 persons per year, and its prevalence is 7.6 to 246.0 cases per 100,000 per year (Danese et al. (2011) N. Engl. J. Med., 365:1713-25). People with UC are at much above average risk of developing colorectal cancer (Eaden et al. (2001) Gut 48:526-35). The colorectal cancer risk is as high as 18% with 30 years of UC. The increased risk of colorectal cancer is due in part to inflammation-induced loss of barrier function. As yet, the causative agent for UC is not known. UC is considered a complex multifactorial disease and it has been hypothesized that autoimmunity, altered microbiome, mucosal barrier compromise and mucosal immunity and genetic factors plays a key role in this disease (Danese et al. (2011) N. Engl. J. Med., 365:1713-25).

UC is associated with defects in intestinal barriers that rely upon cellular tight junctions (TJs) (Das et al. (2012) Virchows Arch. 460:261-70). Identifying genes and proteins that could be targeted to enhance TJs and improve barrier function may lead to new treatment strategies for UC. TJ function may act as a disease modifier in IBD in general. While TJ compromise in the mouse is insufficient to cause intestinal disease, it can drive mucosal immune responses and accelerate the onset and severity of immune-mediated colitis once induced (Su et al. (2009) Gastroenterology 136:551-63). By preventing luminal antigens or infectious microbes from entering the stroma, TJs block unregulated inflammation. Indeed, through their ability to selectively determine intestinal permeability, TJ strongly influence gut physiology and pathophysiology (Madara, J. L. (1998) Annu. Rev. Physiol., 60:143-59).

As yet there are no powerful drugs or therapies to effectively protect against UC. The inflammatory cytokines, TNF-alpha and IFN-gamma, are elevated in ulcerative colitis. While anti-inflammatory drugs and immune suppressors (e.g., TNF alpha inhibitors) are currently prescribed for colitis treatment, side-effects such as risk of opportunistic infections, and the lack of efficacy in certain individuals, limit the quality of treatment (Yapal et al. (2007) Ann. Gastroenterology 20:48-53). Hence there is a need to develop additional immunotherapies to provide protection against colitis.

SUMMARY OF THE INVENTION

In accordance with one aspect of the instant invention, methods for inhibiting, treating, and/or preventing inflammatory disease in patients in need thereof are provided. The methods comprise the administration of at least one antibody or antibody fragment immunologically specific for Bin1, particularly the Myc binding domain. In a particular embodiment, the methods comprise the administration of a composition comprising at least one antibody or antibody fragment immunologically specific for Bin1 and at least one pharmaceutically acceptable carrier. In a particular embodiment, the methods further comprise the administration of at least one other therapeutic agent or method for treating, inhibiting, or preventing the inflammatory bowel disease concurrently and/or sequentially with the at least one antibody or antibody fragment immunologically specific for Bin1.

In accordance with another aspect of the instant invention, methods for inhibiting, treating, and/or preventing colorectal cancer in patients in need thereof are provided. The methods comprise the administration of at least one antibody or antibody fragment immunologically specific for Bin1, particularly the Myc binding domain. In a particular embodiment, the methods comprise the administration of a composition comprising at least one antibody or antibody fragment immunologically specific for Bin1 and at least one pharmaceutically acceptable carrier. In a particular embodiment, the methods further comprise the administration of at least one other therapeutic agent or method for treating, inhibiting, or preventing colorectal cancer concurrently and/or sequentially with the at least one antibody or antibody fragment immunologically specific for Bin1.

In accordance with another aspect of the instant invention, methods for inhibiting, treating, and/or preventing a neurodegenerative disorder, particular a tauopathy, in patients in need thereof are provided. The methods comprise the administration of at least one antibody or antibody fragment immunologically specific for Bin1, particularly the Myc binding domain. In a particular embodiment, the methods comprise the administration of a composition comprising at least one antibody or antibody fragment immunologically specific for Bin1 and at least one pharmaceutically acceptable carrier. In a particular embodiment, the methods further comprise the administration of at least one other therapeutic agent or method for treating, inhibiting, or preventing a neurodegenerative disorder concurrently and/or sequentially with the at least one antibody or antibody fragment immunologically specific for Bin1.

Compositions for the inhibition, treatment, and/or prevention of one of the above diseases are also provided. The compositions comprise at least one Bin1 antibody and at least one pharmaceutically acceptable carrier. The composition may further comprise at least one other agent for the treatment of the ocular disease.

BRIEF DESCRIPTION OF THE DRAWINGS

FIGS. 1A-1G provide images of mouse colon that anti-Bin1 antibody provides protection in a mouse model of colitis. FIG. 1A: Normal mouse colon. FIG. 1B: Colon of mouse fed with 3% DSS. FIG. 1C: Colon of mouse treated with IgG (0.1 mg/mouse), followed by feeding with 3%

DSS. FIG. 1D: Colon of mouse treated with IgG (0.5 mg/mouse), followed by feeding with 3% DSS. FIG. 1E: Colon of mouse treated with anti-Bin1 antibody (0.1 mg/mouse), followed by feeding with 3% DSS. FIGS. 1F and 1G: Colon of mouse treated with Bin1 antibody (0.5 mg/mouse), followed by feeding with 3% DSS.

FIG. 2A: Normal colon with well defined lymphoid follicle. FIGS. 2B-2D: Mice fed with DSS alone (FIG. 2B) or that was treated with IgG (FIGS. 2C and 2D) prior to DSS feeding. Smaller lymphoid follicle in the colon is observed. FIGS. 2E and 2F: Mice treated with the anti-Bin1 antibody and later fed with DSS had an intact lymphoid follicle in the colon.

FIG. 8A) or high dose of tetracycline (10 ug/ml; FIG. 8B).

DETAILED DESCRIPTION OF THE INVENTION

Figure 2C:
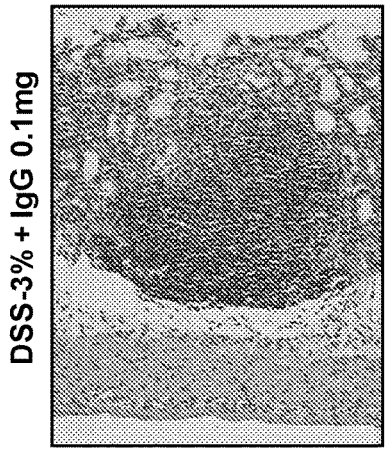
FIGS. 2A-2F show that anti-Bin1 antibody provides protection to the lymphoid follicle in the colon.
Figure 2F:
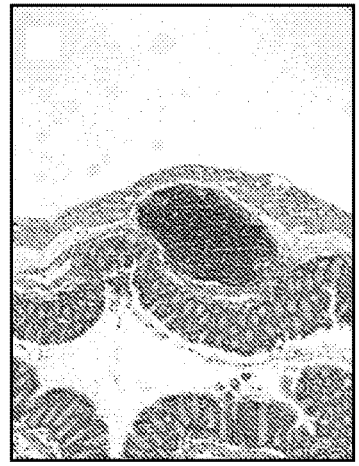
Figure 2B:
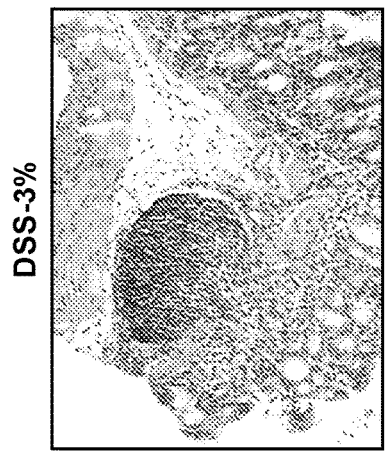
Figure 2E:
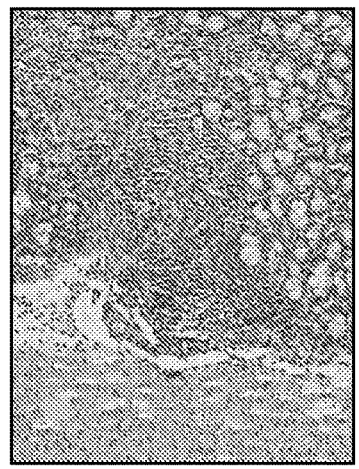
Figure 2A:
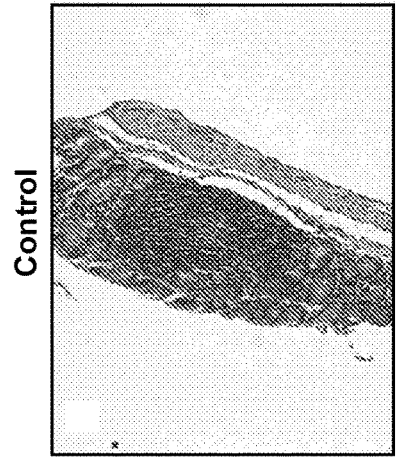
Figure 2D:
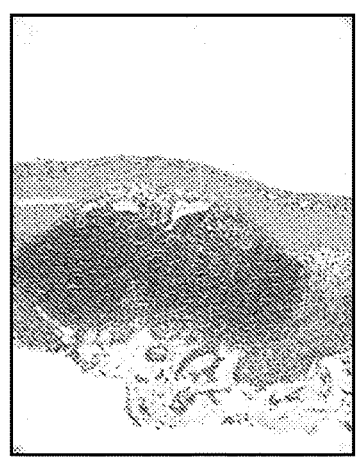

The Bin1 gene encodes a family of BAR (Bin/Amphiphysin/Rvs) adapter proteins that are implicated in membrane and actin dynamics, cell polarity, stress signaling and vesicle trafficking (Prendergast et al. (2009) Biochim. Biophys. Acta, 1795:25-36). Attenuation of the Bin1 gene in a mouse model reduced severity of dextran sodium sulfate (DSS)-induced experimental colitis in a manner associated with an enhancement of epithelial barrier function (Chang et al. (2012) Dig. Dis. Sci., 57:1813-21). Herein, the ability of Bin1 monoclonal antibodies (mAb) to phenocopy effects of genetic attenuation in the colitis model was studied. Novel therapies targeting the Bin1 protein for treatment of inflammatory bowel disease, colorectal cancer, and neurodegenerative diseases are provided.

The present invention provides compositions and methods for the inhibition, prevention, and/or treatment of inflammatory bowel disease. The methods comprise administering at least one anti-Bin1 antibody to a subject. The term "inflammatory bowel disease" refers to a disorder or disease characterized by inflammatory activity (inflammation) in the gastrointestinal tract, particularly inflammatory conditions of the large intestine and/or small intestine. Inflammatory bowel diseases are often chronic conditions of uncertain etiology, characterized by recurrent episodes of abdominal pain, often with diarrhea. Examples of inflammatory bowel diseases include, without limitation: Crohn's disease (also referred to as regional enteritis, terminal ileitis, or granulomatous ileocolitis), colitis (e.g., ulcerative colitis, indeterminate colitis, lymphocytic colitis, ischaemic colitis, diversion colitis, microscopic colitis, infective colitis, or collagenous colitis), Bahcet's syndrome, idiopathic inflammation of the small and/or proximal intestine, and IBD-related diarrhea. In a particular embodiment, the "inflammatory bowel disease" is ulcerative colitis (UC) or Crohn's disease (CD). The methods of the instant invention may further comprise the administration of at least one other therapeutic for the inflammatory bowel disease being treated. Examples of inflammatory bowel disease therapeutics include, without limitation: anti-inflammatory agents, TNF alpha inhibitors (e.g., monoclonal antibodies (e.g., infliximab, adalimumab, certolizumab, and golimumab), receptor fusion proteins (e.g., etanercept)), steroids, aminosalicylates (e.g., balsalazide, mesalamine, olsalazine, sulfasalazine), and immunomodulators or immunosuppressants (e.g., azathioprine, micronutrients (e.g., zinc, berberine)). The agents administered to the subject may be contained within a composition comprising at least one pharmaceutically acceptable carrier. When more than one agent is being administered (e.g., anti-Bin1 antibody with an additional therapeutic), the agents may be administered consecutively (before or after) and/or at the same time (concurrently). The agents may be administered in the same composition or in separate compositions.

The present invention provides compositions and methods for the inhibition, prevention, and/or treatment of cancer. The methods comprise administering at least one anti-Bin1 antibody to a subject. In a particular embodiment, the cancer is colorectal cancer. Colorectal cancer can also be referred to as colon cancer or bowel cancer and includes cancerous growths in the colon, rectum, and/or appendix.

The methods of the instant invention may further comprise the administration of at least one other therapeutic for the cancer being treated. For example, the methods may further comprise the administration of at least one chemotherapeutic agent and/or anti-cancer therapy (e.g., radiation therapy and/or surgery to remove cancerous cells or a tumor (e.g., resection)). The agents administered to the subject may be contained within a composition comprising at least one pharmaceutically acceptable carrier. When more than one agent is being administered (e.g., anti-Bin1 antibody with an additional chemotherapeutic), the agents may be administered consecutively (before or after) and/or at the same time (concurrently). The agents may be administered in the same composition or in separate compositions.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and *Pseudomonas* exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; tubulin interactive agents (e.g., vincristine, vinblastine, and paclitaxel (Taxol®)); and antibodies (e.g., HER2 antibodies (e.g., trastuzumab)).

Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy.

The present invention provides compositions and methods for the inhibition, prevention, and/or treatment of neurodegenerative disease. The methods comprise administering at least one anti-Bin1 antibody to a subject. Examples of neurodegenerative disease include, without limitation, Alzheimer's disease, Parkinson's disease, Lewy Body disease, amyotrophic lateral sclerosis, prion disease, and Huntington's disease. In a particular embodiment, the neurodegenerative disease is a tauopathy. As used herein, "tauopathies" refer to neurodegenerative disorders characterized by neurofibrillary tangles which are primarily composed of abnormal accumulation of phosphorylated or hyperphosphorylated tau proteins. Aberrant phosphorylation of tau is observed in many neurodegenerative disorders. Examples of tauopathies are provided in Lee et al. (Ann. Rev. Neurosci. (2001) 201:1121-1159). Examples of tauopathies include, without limitation: Alzheimer's disease, amyotrophic lateral sclerosis/parkinsonism-dementia complex, argyrophilic grain dimentia, corticobasal degeneration, Creutzfeldt-Jakob disease, dementia pugilistic, diffuse neurofibrillary tangles with calcification, Down's syndrome, frontotemporal dementia, parkinsonism linked to chromosome 17, Gerstmann-Straussler-Scheinker disease, Hallervorden-Spatz disease, myotonic dystrophy, Niemann-Pick disease, non-Guamanian motor neuron disease with nerofibrillary tangles, Pick's disease, Huntington's disease, postencephilitic parkinsonism, prion protein cerebral amyloid angiopathy, progressive subcortical gliosis, progressive supranuclear palsy, subacute sclerosing panencephalitis, sporadic corticobasal degeneration, and tangle only dementia. In a particular embodiment, the tauopathy is Alzheimer's disease.

The methods of the instant invention may further comprise the administration of at least one other therapeutic for the neurodegenerative disorder being treated. For example, the methods may further comprise the administration of at least one other therapeutic agent. Examples of neurodegenerative disorder therapeutics include, without limitation: cholinesterase inhibitors (e.g., donepezil, galantamine, rivastigmine) and N-methyl D-aspartate (NMDA) antagonists (e.g., amantadine, memantine). The agents administered to the subject may be contained within a composition comprising at least one pharmaceutically acceptable carrier. When more than one agent is being administered (e.g., anti-Bin1 antibody with an additional therapeutic), the agents may be administered consecutively (before or after) and/or at the same time (concurrently). The agents may be administered in the same composition or in separate compositions.

As stated hereinabove, the methods (and compositions) of the instant invention comprise administering at least one antibody or antibody fragment which is immunologically specific for Bin1 (bridging integrator 1; anti-Bin1 antibody) to a subject. In a particular embodiment, the anti-Bin1 antibody is immunologically specific for human Bin1. Amino acid and nucleotide sequences of human Bin1 and its isoforms/variants are provided in GenBank Gene ID: 274. An exemplary amino acid sequence of human Bin1 (e.g., 451 amino acids) is:

```
                                              (SEQ ID NO: 1)
Met Leu Trp Asn Val Val Thr Ala Gly Lys Ile Ala

Ser Asn Val Gln Lys Lys Leu Thr Arg Ala Gln Glu

Lys Val Leu Gln Lys Leu Gly Lys Ala Asp Glu Thr

Lys Asp Glu Gln Phe Glu Gln Cys Val Gln Asn Phe

Asn Lys Gln Leu Thr Glu Gly Thr Arg Leu Gln Lys

Asp Leu Arg Thr Tyr Leu Ala Ser Val Lys Ala Met

His Glu Ala Ser Lys Lys Leu Asn Glu Cys Leu Gln

Glu Val Tyr Glu Pro Asp Trp Pro Gly Arg Asp Glu

Ala Asn Lys Ile Ala Glu Asn Asn Asp Leu Leu Trp

Met Asp Tyr His Gln Lys Leu Val Asp Gln Ala Leu

Leu Thr Met Asp Thr Tyr Leu Gly Gln Phe Pro Asp

Ile Lys Ser Arg Ile Ala Lys Arg Gly Arg Lys Leu
```

-continued

```
Val Asp Tyr Asp Ser Ala Arg His His Tyr Glu Ser

Leu Gln Thr Ala Lys Lys Lys Asp Glu Ala Lys Ile

Ala Lys Ala Glu Glu Leu Ile Lys Ala Gln Lys

Val Phe Glu Glu Met Asn Val Asp Leu Gln Glu Glu

Leu Pro Ser Leu Trp Asn Ser Arg Val Gly Phe Tyr

Val Asn Thr Phe Gln Ser Ile Ala Gly Leu Glu Glu

Asn Phe His Lys Glu Met Ser Lys Leu Asn Gln Asn

Leu Asn Asp Val Leu Val Gly Leu Glu Lys Gln His

Gly Ser Asn Thr Phe Thr Val Lys Ala Gln Pro Arg

Lys Lys Ser Lys Leu Phe Ser Arg Leu Arg Arg Lys

Lys Asn Ser Asp Asn Ala Pro Ala Lys Gly Asn Lys

Ser Pro Ser Pro Pro Asp Gly Ser Pro Ala Ala Thr

Pro Glu Ile Arg Val Asn His Glu Pro Glu Pro Ala

Gly Gly Ala Thr Pro Gly Ala Thr Leu Pro Lys Ser

Pro Ser Gln Pro Ala Glu Ala Ser Glu Val Ala Gly

Gly Thr Gln Pro Ala Ala Gly Ala Gln Glu Pro Gly

Glu Thr Ala Ala Ser Glu Ala Ala Ser Ser Ser Leu

Pro Ala Val Val Val Glu Thr Phe Pro Ala Thr Val

Asn Gly Thr Val Glu Gly Gly Ser Gly Ala Gly Arg

Leu Asp Leu Pro Pro Gly Phe Met Phe Lys Val Gln

Ala Gln His Asp Tyr Thr Ala Thr Asp Thr Asp Glu

Leu Gln Leu Lys Ala Gly Asp Val Val Leu Val Ile

Pro Phe Gln Asn Pro Glu Glu Gln Asp Glu Gly Trp

Leu Met Gly Val Lys Glu Ser Asp Trp Asn Gln His

Lys Lys Leu Glu Lys Cys Arg Gly Val Phe Pro Glu

Asn Phe Thr Glu Arg Val Pro.
```

In a particular embodiment, the amino acid sequence of Bin1 has at least 80%, 85%, 90%, 95%, 97%, 99%, or 100% homology or identity with SEQ ID NO: 1.

In a particular embodiment, the anti-Bin1 antibody is immunologically specific for an exon 13-encoded splice isoform of Bin1 (see, e.g., DuHadaway et al. (J. Cell Biochem. (2003) 88:635-642). In a particular embodiment, the anti-Bin1 antibody is immunologically specific for the Myc-binding domain of Bin1 (e.g., amino acids 270-383 of SEQ ID NO: 1). In a particular embodiment, the anti-Bin1 antibody is immunologically specific for an amino acid sequence having at least 90%, 95%, 97%, 99%, or 100% homology or identity with the sequence (or an epitope within) [323-356]:

```
                                         (SEQ ID NO: 2)
Ala Gly Gly Thr Gln    Pro Ala Ala Gly Ala

Gln Glu Pro Gly Glu    Thr Ala Ala Ser Glu

Ala Ala Ser Ser Ser    Leu Pro Ala Val Val

Val Glu Thr Phe.
```

In a particular embodiment, the anti-Bin1 antibody is an anti-Bin1 monoclonal described in U.S. Pat. No. 6,048,702, incorporated by reference herein for the description of the anti-Bin1 antibodies. In a particular embodiment, the anti-Bin1 antibody is anti-Bin1 monoclonal antibody 99D (described in U.S. Pat. No. 6,048,702, incorporated herein by reference, particularly for the anti-Bin1 antibodies, particularly 99D). Hybridomas secreting monoclonal antibody 99D have been deposited with the American Type Culture Collection (ATCC HB-12580).

The antibodies of the instant invention may be naturally occurring or synthetic or modified (e.g., a recombinantly generated antibody; a chimeric antibody; a bispecific antibody; a humanized antibody; a camelid antibody; and the like). The antibody may comprise at least one purification tag. In a particular embodiment, the antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment. In a particular embodiment of the instant invention, the antibody comprises an Fc region. In a particular embodiment of the instant invention, the antibody is a monoclonal antibody.

The instant invention also encompasses synthetic proteins which mimic an immunoglobulin. Examples include, without limitation, Affibody® molecules (Affibody, Bromma, Sweden), darpins (designed ankyrin repeat proteins; Kawe et al. (2006) J. Biol. Chem., 281:40252-40263), and peptabodies (Terskikh et al. (1997) PNAS 94:1663-1668).

The antibodies of the instant invention may be further modified. For example, the antibodies may be humanized. In a particular embodiment, the hybrid antibodies (or a portion thereof) are inserted into the backbone of an antibody or antibody fragment construct. For example, the variable light domain and/or variable heavy domain of the antibodies of the instant invention may be inserted into another antibody construct. Methods for recombinantly producing antibodies are well-known in the art. Indeed, commercial vectors for certain antibody and antibody fragment constructs are available.

The antibodies of the instant invention may also be conjugated/linked to other components. For example, the antibodies may be operably linked (e.g., covalently linked, optionally, through a linker) to at least one detectable agent, imaging agent, contrast agent, or therapeutic compound (e.g., see above). The antibodies of the instant invention may also comprise at least one purification tag (e.g., a His-tag).

The antibody molecules of the invention may be prepared using a variety of methods known in the art. Polyclonal and monoclonal antibodies may be prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells. In one embodiment of the invention, the antibody molecules are produced by expression of recombinant antibody or antibody fragments in host cells. The nucleic acid molecules encoding the antibody may be inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Compositions comprising at least one anti-Bin1 antibody are also encompassed by the instant invention. In a particular embodiment, the composition comprises at least one anti-Bin1 antibody or antibody fragment and at least one pharmaceutically acceptable carrier. The composition may further comprise at least one other therapeutic compound for the inhibition, treatment, and/or prevention of the disease or disorder to be treated (see, e.g., hereinabove). Alternatively, at least one other therapeutic compound may be contained within a separate composition(s) with at least one pharmaceutically acceptable carrier. The present invention also encompasses kits comprising a first composition comprising at least one anti-Bin1 antibody or antibody fragment and a second composition comprising at least one other therapeutic compound for the inhibition, treatment, and/or prevention of the disease or disorder to be treated. The first and second compositions may further comprise at least one pharmaceutically acceptable carrier.

As explained hereinabove, the compositions of the instant invention are useful for treating an inflammatory bowel disease, a neurodegenerative disorder, and/or colorectal cancer. A therapeutically effective amount of the composition may be administered to the subject. The dosages, methods, and times of administration are readily determinable by persons skilled in the art, given the teachings provided herein.

The antibodies as described herein will generally be administered to a patient as a pharmaceutical preparation. The term "patient" as used herein refers to human or animal subjects. These antibodies may be employed therapeutically, under the guidance of a physician for the treatment of the indicated disease or disorder.

The pharmaceutical preparation comprising the antibody molecules of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of an antibody according to the invention that is suitable for administration to a particular patient may be determined by a physician considering the patient's age, sex, weight, general medical condition, and the specific condition and severity thereof for which the antibody is being administered. The physician may also consider the route of administration of the antibody, the pharmaceutical carrier with which the antibody may be combined, and the antibody's biological activity.

Selection of a suitable pharmaceutical preparation depends upon the method of administration chosen. For example, the antibodies of the invention may be administered by direct injection into any desired tissue or into the surrounding area. In this instance, a pharmaceutical preparation comprises the antibody molecules dispersed in a medium that is compatible with the target tissue.

Antibodies may also be administered parenterally, by intravenous injection into the blood stream, or by subcutaneous, intramuscular or intraperitoneal injection. Pharmaceutical preparations for parenteral injection are known in the art. If parenteral injection is selected as a method for administering the antibodies, steps must be taken to ensure that sufficient amounts of the molecules reach their target cells to exert a biological effect. The lipophilicity of the antibodies, or the pharmaceutical preparation in which they are delivered, may have to be increased so that the molecules can arrive at their target locations. Furthermore, the antibodies may have to be delivered in a cell-targeting carrier so that sufficient numbers of molecules will reach the target cells. Methods for increasing the lipophilicity of a molecule are known in the art. If a small form of the antibody is to be administered, including but not limited to a Fab fragment, a Dab, an scFv or a diabody, it may be conjugated to a second (carrier) molecule such as, but not limited to polyethylene glycol (PEG) or an albumin-binding antibody or peptide to prolong its retention in blood.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of anti-Bin1 antibody molecules may be determined by evaluating the toxicity of the antibody molecules in animal models. Various concentrations of antibody pharmaceutical preparations may be administered to murine models of the disease or disorder and the minimal and maximal dosages may be determined based on the results and side effects as a result of the treatment. Appropriate dosage unit may also be determined by assessing the efficacy of the antibody molecule treatment in combination with other standard drugs. The dosage units of anti-Bin1 antibody molecules may be determined individually or in combination with another treatment.

The pharmaceutical preparation comprising the anti-Bin1 antibody molecules may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The methods of the instant invention may further comprise monitoring the disease or disorder in the subject after administration of the composition(s) of the instant invention to monitor the efficacy of the method.

Definitions

The following definitions are provided to facilitate an understanding of the present invention:

The singular forms "a," "an," and "the" include plural referents unless the context clearly dictates otherwise.

A "therapeutically effective amount" of a compound or a pharmaceutical composition refers to an amount effective to prevent, inhibit, treat, or lessen the symptoms of a particular disorder or disease. The treatment of an ocular disorder herein may refer to curing, relieving, and/or preventing the ocular disorder, the symptom of it, or the predisposition towards it.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including mammals such as humans.

The terms "immunosuppressant" and "immunosuppressive agent", as used herein, include compounds or compositions which suppress immune responses or the symptoms associated therewith. Immunosuppressant include, without limitation, purine analogs (e.g., azathioprine), methotrexate, cyclosporine (e.g., cyclosporin A), cyclophosphamide, leflunomide, mycophenolate (mycophenolate mofetil), steroids (e.g., glucocorticoid, corticosteroid), methylprednisone, prednisone, non-steroidal anti-inflammatory drug (NSAID), chloroquine, hydroxycloroquine, chlorambucil, CD20 antagonist (e.g., rituximab, ocrelizumab, veltuzumab or ofatumumab), abatacept, a TNF antagonist (e.g., infliximab, adalimumab, etanercept), macrolides (e.g., pimecrolimus, tacrolimus (FK506), and sirolimus), dehydroepiandrosterone, lenalidomide, a CD40 antagonist (e.g., anti-CD40L antibodies), abetimus sodium, BLys antagonists (e.g., anti-BLyS (e.g., belimumab), dactinomycin, bucillamine, penicillamine, leflunomide, mercaptopurine, pyrimidine analogs (e.g., cytosine arabinoside), mizoribine, alkylating agents (e.g., nitrogen mustard, phenylalanine mustard, buslfan, and cyclophosphamide), folic acid antagonsists (e.g., aminopterin and methotrexate), antibiotics (e.g., rapamycin, actinomycin D, mitomycin C, puramycin, and chloramphenicol), human IgG, antilymphocyte globulin (ALG), antibodies (e.g., anti-CD3 (OKT3), anti-CD4 (OKT4), anti-CD5, anti-CD7, anti-IL-2 receptor (e.g., daclizumab and basiliximab), anti-alpha/beta TCR, anti-ICAM-1, muromonab-CD3, anti-IL-12, alemtuzumab and antibodies to immunotoxins), and derivatives and analogs thereof.

As used herein, an "anti-inflammatory agent" refers to compounds for the treatment of an inflammatory disease or the symptoms associated therewith. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

The following example is provided to illustrate various embodiments of the present invention. The example is not intended to limit the invention in any way.

EXAMPLE

A DSS model of colitis (Chang et al. (2012) Dig. Dis. Sci., 57:1813-21) was used herein to evaluate the efficacy of the Bin1 mAb. Briefly, for the DSS model, mice were administered 3% dextran sodium sulfate (DSS, MW 36-50 kDa) in drinking water. Mice treated with an anti-Bin1 antibody (monoclonal 99D) were protected on a histological basis from DSS-induced colitis compared to control mice. Severe lesions were observed throughout the colonic mucosa of DSS-treated mice that were uninjected or injected with murine IgG, with high levels of neutrophil and lymphocyte infiltration into the mucosal and submucosal areas, and loss of crypt architecture in the mucosa (FIG. 1B-E). In contrast, mice treated with high-dose anti-Bin1 antibody exhibited more normal colon mucosa similar to untreated controls (FIG. 1F-G). Table 1 summarizes the intensity of colon erosion in each group as determined by a longitudinal evaluation of histologically stained tissues obtained from the mice.

TABLE 1

Intensity of colon erosion for indicated treatment groups.

| Treatment | Degree of Erosion |
| --- | --- |
| Control | 0 |
| DSS (3%) | +++++ |
| IgG (0.1 mg) | +++++ |
| IgG (0.5 mg) | +++++ |
| Bin1 (0.1 mg) | +++++ |
| Bin1 (0.5 mg) | + |

Apart from defective intestinal barriers, the major hallmark of colitis is inflammation with recruitment of lymphocytes and neutrophils to the lamina propria. Gut-associated lymphoid tissue (GALT), which appears as lymphoid follicles, is involved in unique inflammatory phenomena and luminal antigen sampling in the colon. Histological evaluations revealed ruptures in the lymphoid follicles in colons from mice receiving DSS alone or DSS+nonspecific murine IgG. Lymphocytes and neutrophils were likewise seen in the mucosal layer consistent with inflammatory migration. However, lymphoid follicles were intact in mice receiving DSS+anti-Bin1 antibody (FIG. 2). These observations indicate that anti-Bin1 antibody administration protects the lymphoid follicle and limits inflammation, likely by directly improving barrier function.

Monoclonal antibody 99D recognizes an epitope within the C-terminal Myc-binding domain encoded by Bin1 exon 13. Since this exon is alternately spliced in the two protein isoforms expressed by all cell types, 99D recognizes only one of the two Bin1 isoform(s) which are expressed in colonic epithelial cells (DuHadaway et al., (2003) J. Cell. Biochem., 88:635-42). In contrast, monoclonal antibody 2F11 recognizes an epitope within the N-terminal BAR domain encoded by Bin1 exons 7 and 8 (DuHadaway et al., (2003) J. Cell. Biochem., 88:635-42). As such, 2F11 is a "pan-isoform" anti-Bin1 mAb. The 99D and 2F11 mAbs recognize both human and mouse Bin1. However, unlike 99D, 2F11 did not prevent colitis like 99D. Thus, in the studies presented below, 99D was used to explore functional effects on TJ parameters, while 2F11 was used only for expression analyses.

To evaluate the cellular effects of anti-Bin1 antibodies and the functional mechanisms, the well-described human colonic epithelial cell culture model Caco-2 was used. At confluence, Caco-2 cell layers will form functional TJ with effective barrier function. In differentiated Caco-2 cells (11 days at confluence in maintenance media), reduced Bin1 expression was observed—as detected by 2F11 on Western blots—if cells were incubated with the 99D antibody. The results indicate that 99D may phenocopy Bin1 genetic attenuation in colon cells.

Figure 3A:
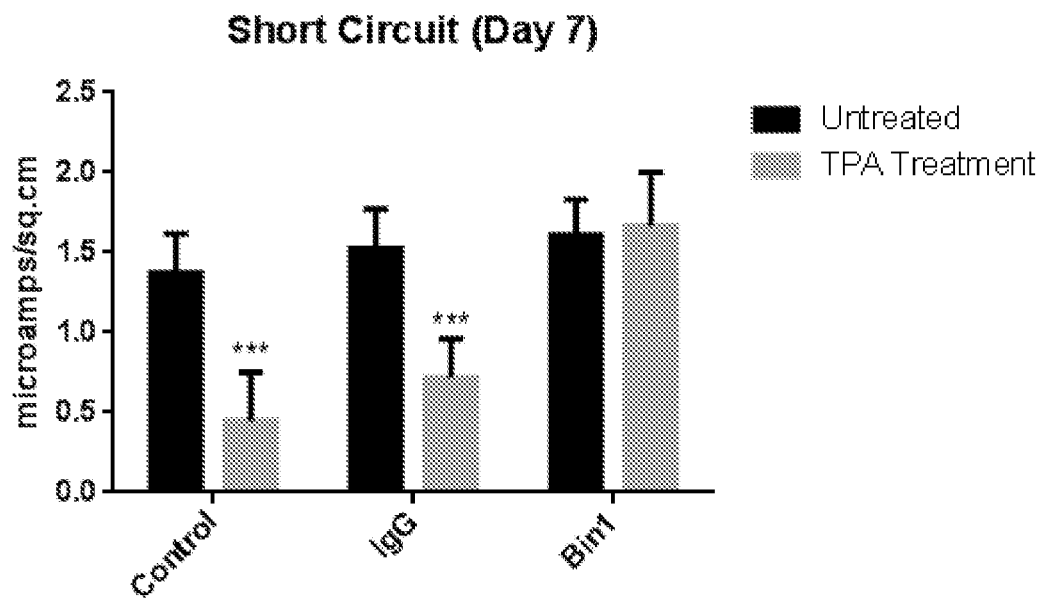
FIGS. 3A and 3B show that Caco-2 cells treated with anti-Bin1 antibody had increased short circuit current compared to the IgG control. There was no change in short circuit current on day 7 (FIG. 3A) and on day 11 (FIG. 3B) when Caco-2 cells treated with Bin1 were exposed to TPA. ***$p<0.0001$, as determined by ANOVA.
Figure 3B:
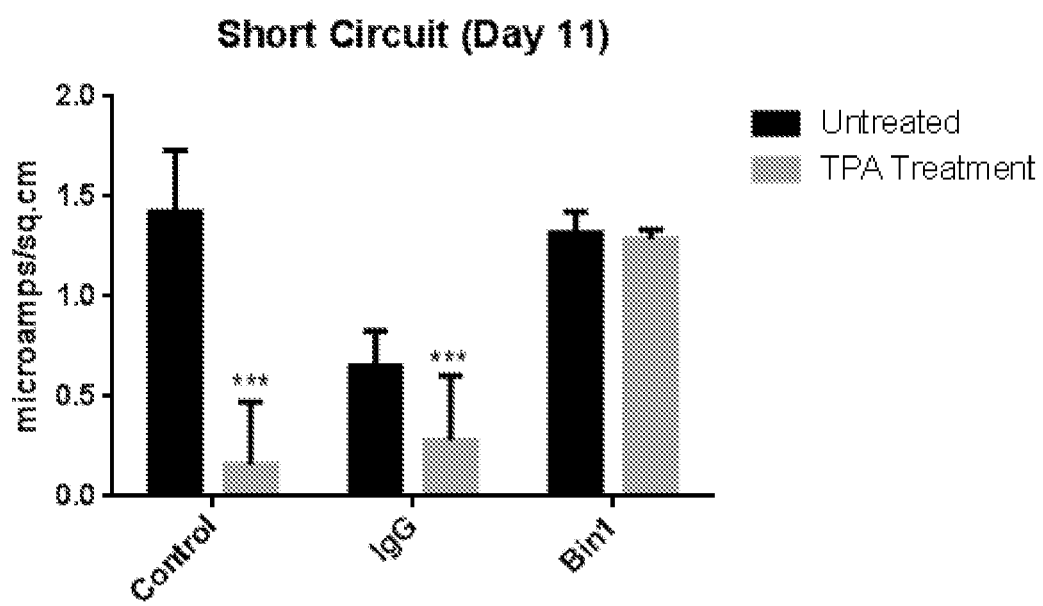

UC is characterized by a defective intestinal barrier function arising from the abnormal leakiness of cellular TJs, which may act as a disease modifier in this setting. In epithelial cells, TJs act to separate the apical (lumen) and basolateral (interstitium) fluid compartments, thereby serving as a selective permeable barrier for paracellular diffusion. TJs define epithelial organization and are formed by occludin and the claudins, the assembly of which establishes the paracellular barrier controlling the flow of molecules in the intercellular space between the cells of an epithelium. Claudins interact with intracellular scaffolding proteins of the TJ complex, such as ZO-1. In particular, claudin-2 has an important role in forming a paracellular channel that affects specific permeability for small cations across TJs. The Caco-2 cell model was used to investigate the in vitro effects of 99D on paracellular permeability and TJ protein (claudin) expression. To mimic an inflammatory stimulus, cells were incubated briefly (4 hours) with the phorbol ester 12-O-tetradecanoylphorbol-13-acetate (TPA). Confluent Caco-2 cell cultures were treated with 99D or IgG for 11 days in the absence or presence of an inflammatory stimulus. Caco-2 cell layers treated with 99D through the period of confluence-induced differentiation exhibited variable changes in paracellular resistance, but a consistent effect on short circuit current, countering the inhibitory effects of TPA (FIG. 3).

Figure 4:
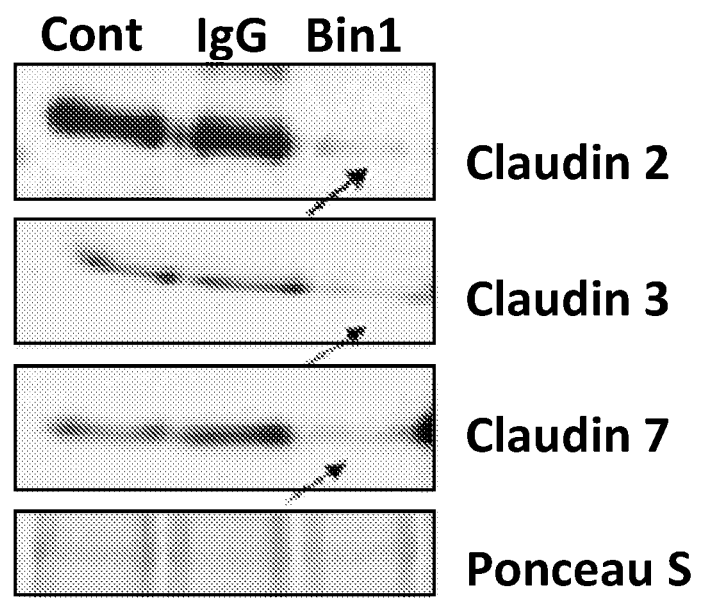
FIG. 4 shows the expression of claudins in Caco-2 cells after treatment with Bin-1 antibody. Arrows indicate downregulation of claudins-2, -3 and -7 when treated with anti-Bin1 monoclonal antibody.

The steady-state level of the TJ proteins, claudins-2, -3, and -7, was compared in Caco-2 cell layers that were untreated or treated with murine IgG or 99D mAb. Treatment with 99D reduced levels of all the claudins analyzed (FIG. 4). In cells exposed to TPA, strongly elevated expression of all claudins analyzed was observed.

Figure 5A:
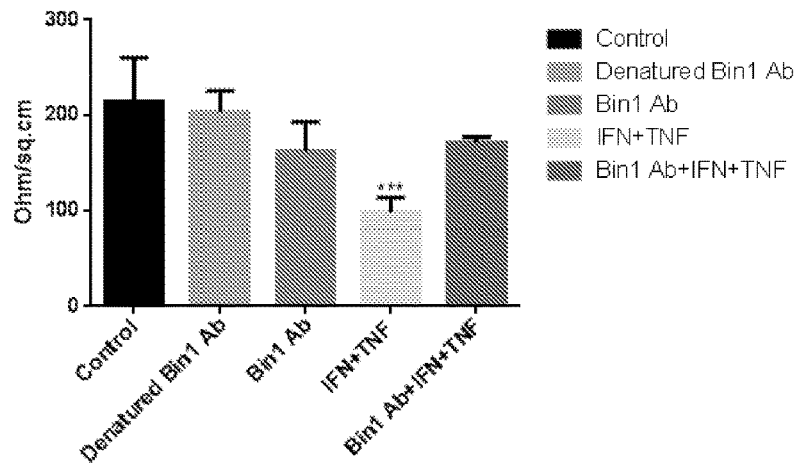
FIGS. 5A-5C show the electrophysiology of Caco-2 cells treated with cytokines. Anti-Bin1 antibody treated Caco-2 cells incubated in the presence of the cytokines TNF-alpha and IFN-gamma had high resistance (FIG. 5A), short circuit (FIG. 5B), and low mannitol flux (FIG. 5C).
Figure 5B:
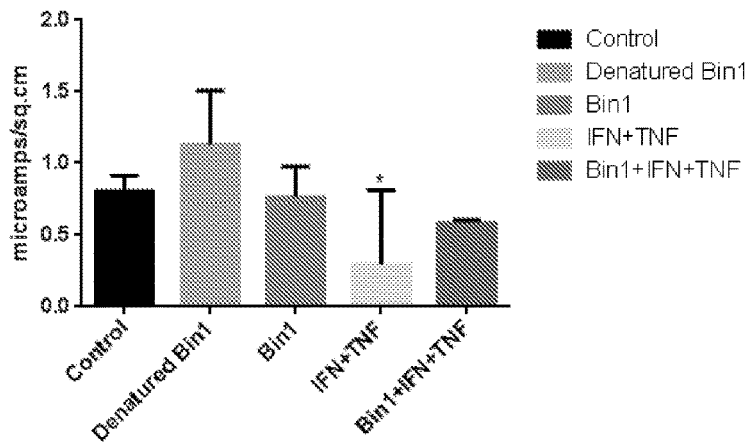
Figure 5C:
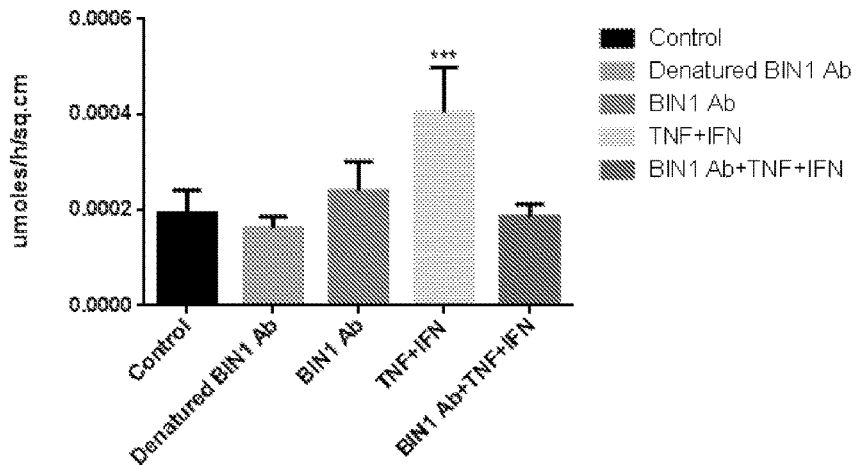
Figure 6:
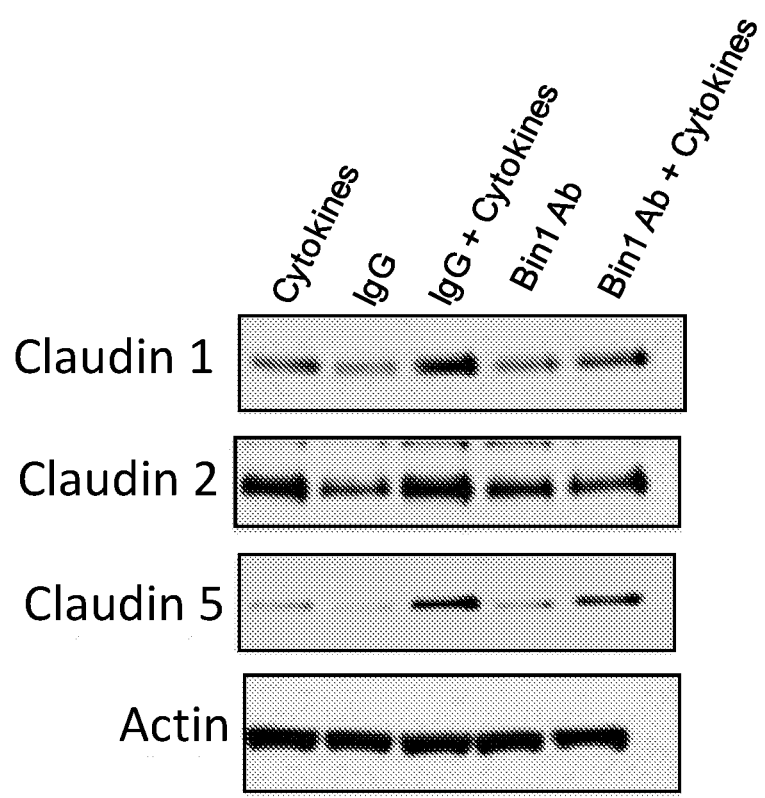
FIG. 6 shows the expression of claudins in anti-Bin1 antibody treated Caco-2 cells after exposure to cytokines. The claudins-2, -3 and -7 were downregulated when treated with anti-Bin1 antibody.

TNF-α and IFN-γ are proinflammatory cytokines involved in UC. A study was conducted to determine how these cytokines influence Caco-2 cells in the presence and absence of anti-Bin1 antibody. When exposed to the cytokines, Caco-2 cell layers that had been pre-treated with anti-Bin1 antibody had significantly higher resistance (FIG. 5A). The degree of leakiness of these cell layers was determined using radiolabeled D-mannitol. Anti-Bin1 antibody treated Caco-2 cell layers exposed to the cytokines had less mannitol leak compared to cytokine-treated Caco-2 cell layers alone (high leakage) (FIG. 5C). The experiments demonstrate that in the presence of the anti-Bin1 antibody, cellular TJs were not compromised after exposure to inflammatory cytokines. The expression of the claudin proteins was also analyzed after exposure to the cytokines. There were no changes in the levels of claudins-3, -4 and -7 as well as occludin expression between treatments with cytokines. However, claudins-1, -2, and -5 were altered by cytokine exposure. Anti-Bin1 antibodies prevented the decrease in these proteins after exposure to the cytokines (FIG. 6).

Figure 7:
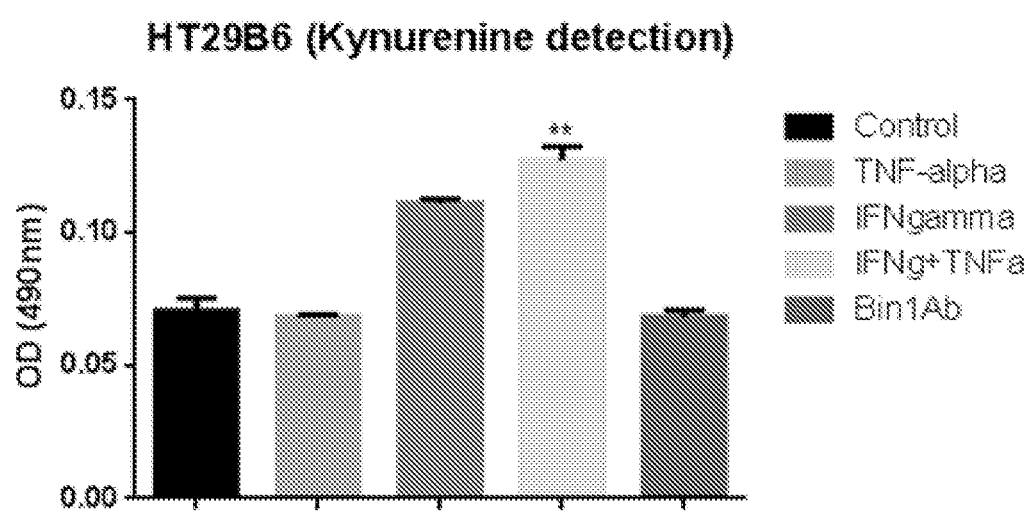
FIG. 7 shows that anti-Bin1 antibody treatment does not increase the level of kynurenine expression in HT29B6 cells. The cytokine IFN gamma and the combination of IFN gamma and TNF-alpha increase the levels of kynurenine in HT29B6 cells, whereas anti-Bin1 antibody does not increase the levels of kynurenine expression.

Indoleamine 2,3 dioxygenase 1 (IDO1) is a heme containing enzyme that catalyzes the rate limiting step in tryptophan catabolism to formylkynurenine. IDO activity modulates the character of inflammatory responses in the tissue microenvironment to support carcinogenesis (Prendergast et al. (2010) Am. J. Pathol., 176:2082-7). IDO suppresses the function of T effector cells, favors differentiation of T regulatory cells and is considered as a mediator of immune escape in cancer. In some tissues, loss of Bin1 leads to increase in expression of IDO1 (Muller et al. (2005) Cancer Res., 65:8065-8). To explore whether reduction in Bin1 leads to increase in IDOL HT29B6 cells (human colonic epithelial cell line) were treated with anti-Bin1 antibody. The increase in IDO1 was monitored by analyzing the expression of kynurenine levels. When HT29 B6 cells were incubated with the anti-Bin1 antibody there was no increase in levels of kynurenine (FIG. 7). The results demonstrated that treatment with anti-Bin1 antibody does not induce IDO1 and, therefore, does not favor tumor microenvironment. In view of these results, the anti-Bin1 antibody can be used in the treatment of colitis and colorectal cancer.

Alzheimer's disease (AD), the most common cause of dementia, is a progressive, neurodegenerative brain disease of unknown etiology that primarily affects the elderly. As yet there are no effective medications to prevent or treat AD (Zhu et al. (2006) Clin. Interv. Aging 1:143-154). AD is characterized pathologically by extracellular deposits of amyloid beta (Aβ) and by neurofibrillary tangles and neuropil threads composed of hyperphosphorylated filaments of the otherwise microtubule-associated protein Tau. Although Aβ is apparently the initiator in AD pathogenesis, it has become increasingly clear that aberrant Tau protein also plays a key role. Disturbed insulin signaling cascade may be implicated in the pathways through which soluble Aβ induces tau phosphorylation and further indicate that correcting insulin signal dysregulation in AD may offer a potential therapeutic approach (Tokutake et al. (2012) J. Biol. Chem., 287:35222-35233).

Tau deposition is seen in several neurodegenerative diseases including, without limitation, frontotemporal dementia, Pick disease, dementia pugilistica, corticobasal degeneration, and progressive supranuclear palsy. In these disorders, collectively called tauopathies, aberrant Tau is the principal pathological feature. The identification of tau mutations that cause familial dementia demonstrated that aberrant Tau alone could cause neurodegenerative disease. Tau also plays a major role in Alzheimer's disease (AD) (Wolfe, M. S. (2009) J. Biol. Chem., 284: 6021-6025).

AD etiology is influenced by complex interactions between genetic and environmental risk factors. Mutations in the amyloid precursor protein, presenlin 1 and 2 genes, have been associated with the early-onset familial form of AD. Additionally, the apolipoprotein E (APOE) gene is a susceptibility polymorphism for late-onset AD, the most common form of AD and the most common dementia in the aging population. The APOE ε4 allele increases the risk of developing AD but is neither necessary nor sufficient to cause AD, and genetic testing for APOE cannot be interpreted as a definitive predictor (Cassidy et al. (2008) Alzheimers Dement. 4:406-413).

BIN1 has been implicated in sporadic Alzheimer's disease (AD) by a number of genome wide association studies (GWAS) in a variety of populations (Seshadri et al. (2010) JAMA 303:1832-1840). BIN1 has also been identified as a genetic determinant of AD (Lambert et al. (2011) Neurobiol. Aging 32:756.e11-5). A meta-analysis using a genome-wide association study has also identified multiple variants at the Bin1 locus associated with AD (Hu et al. (2011) PLoS One 6:e16616). Further, BIN1 expression levels have been associated with disease progression, where higher expression was associated with a delayed age at onset (Karch et al. (2012) PLoS One 7:e50976). BIN1 transcript levels are increased in AD brains and a novel 3 bp insertion allele ~28 kb upstream of BIN1 has been identified which increased transcriptional activity in vitro (Chapuis et al. (2013) Mol. Psychiatry 18:1225-34). Tau and BIN1 colocalized and interacted in human neuroblastoma cells and in mouse brain and BIN1 may mediate AD risk by modulating Tau pathology (Chapuis et al. (2013) Mol. Psychiatry 18:1225-34).

There are at least 15 different known isoforms of BIN1, with many being expressed in the brain including the longest isoform (iso1), which is brain-specific and localizes to axon initial segments and nodes of Ranvier. The amount of the largest isoform of BIN1 is significantly reduced in the AD brain compared to age-matched controls and smaller BIN1 isoforms are significantly increased (Holler et al. (2014) J, Alzheimers Dis., 42:1221-1227). Further, BIN1 was significantly correlated with the amount of neurofibrillary tangle (NFT) pathology, but not with either diffuse or neuritic plaques or with the amount of amyloid-β peptide. BIN1 is known to be abnormally expressed in another human disease, myotonic dystrophy, which also features prominent NFT pathology. These data indicate that BIN1 is involved in AD as a modulator of NFT pathology and other human diseases that feature tau pathology.

Figure 8A:
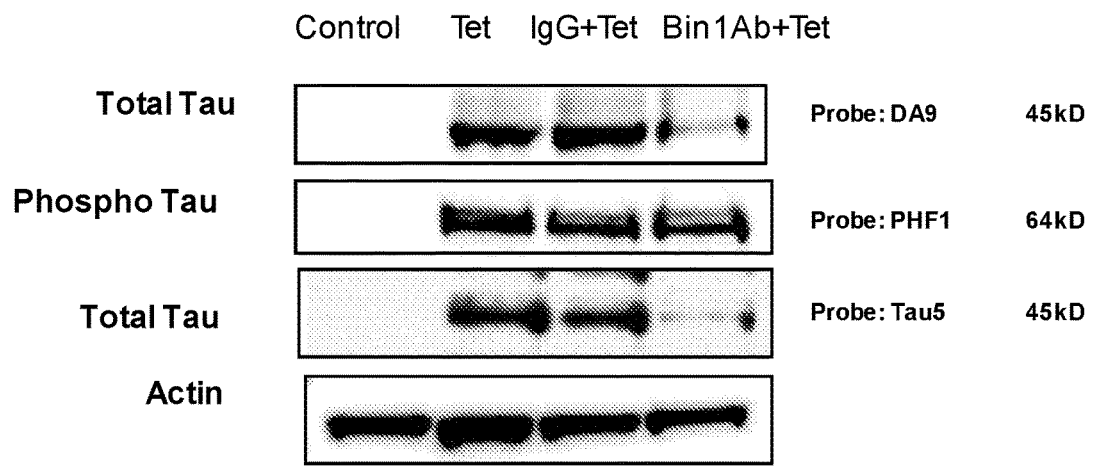
FIGS. 8A and 8B show that anti-Bin1 antibody treatment decreases Tau expression in cell culture. Anti-Bin1 antibody (0.05 mg/ml) treated HEK 293 T-REx™ cells had low expression of total tau and phosphorylated tau after induction of tau with low dose of tetracycline (1 ug/ml.
Figure 8B:
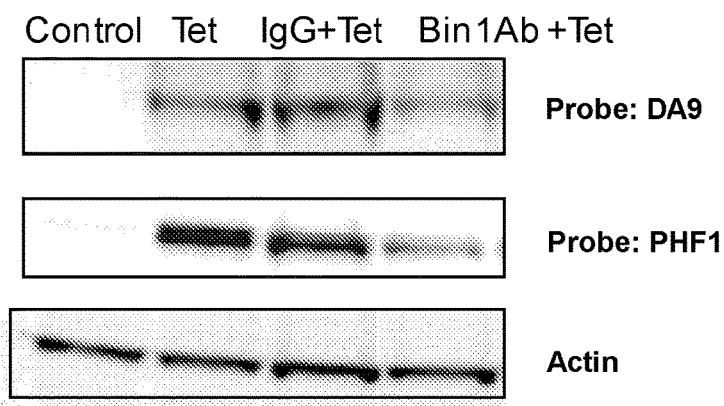
Figure 9A:
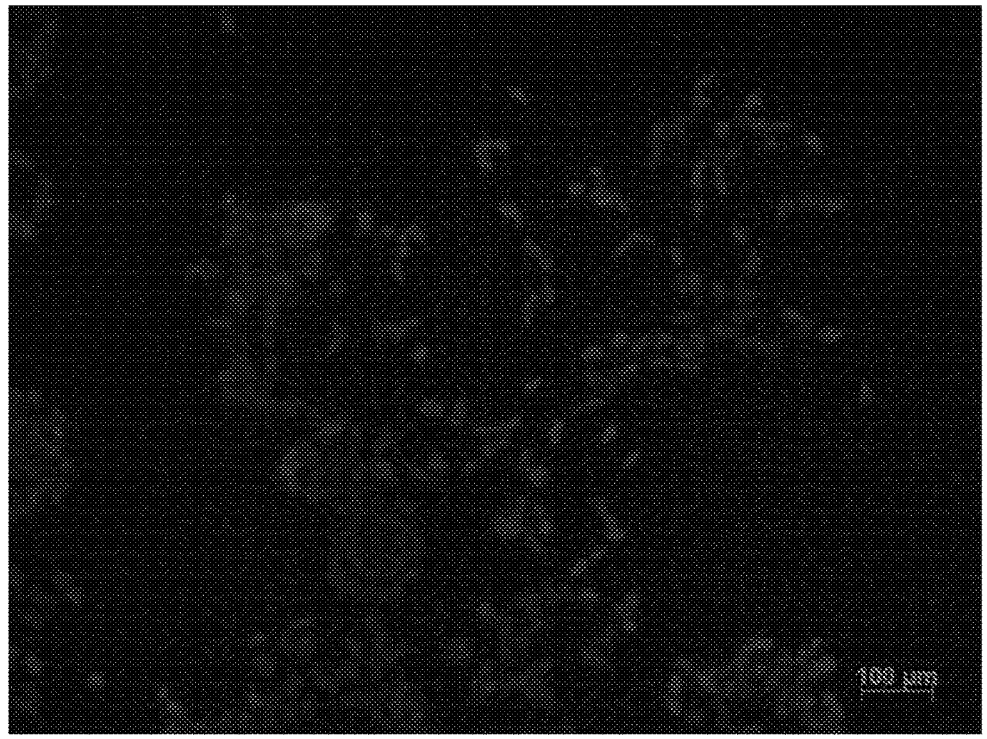
FIGS. 9A-9D show that anti-Bin1 antibody treatment decreases Tau expression in cell culture as determined by microscopy. Untreated HEK 293 T-REx™ cells (FIG. 9A), HEK 293 T-REx™ cells treated with tetracycline (1 ug/ml) to induce Tau (FIG. 9B), HEK 293 T-REx™ cells treated with IgG (0.05 mg/ml) and tetracycline (1 ug/ml) (FIG. 9C, and HEK 293 T-REx™ cells treated with Bin1 mAb (0.05 mg/ml) and tetracycline (1 ug/ml) (FIG. 9D) were examined. The nucleus was stained with DAPI and Tau was stained with Cy3 (Probe DA9 antibody).
Figure 9B:
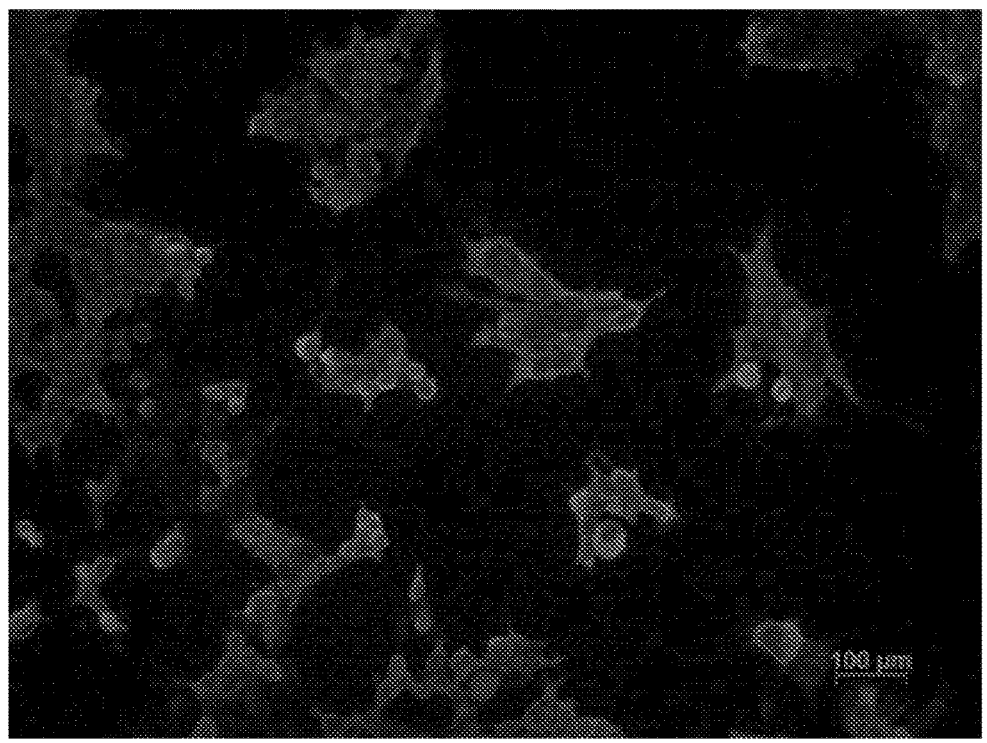
Figure 9C:
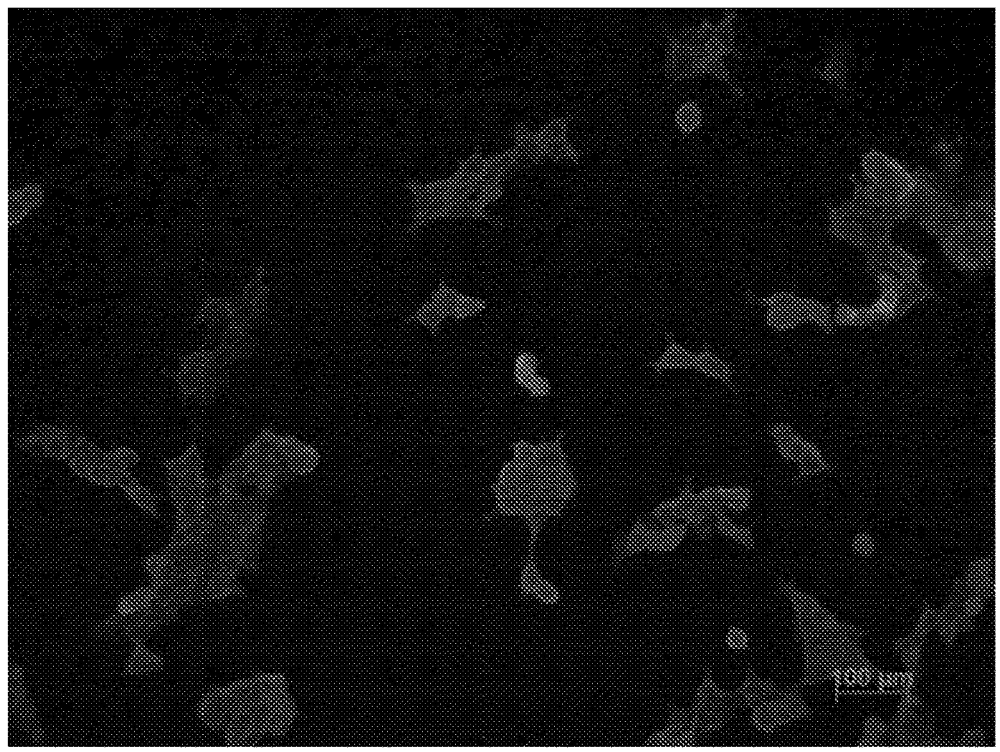
Figure 9D:
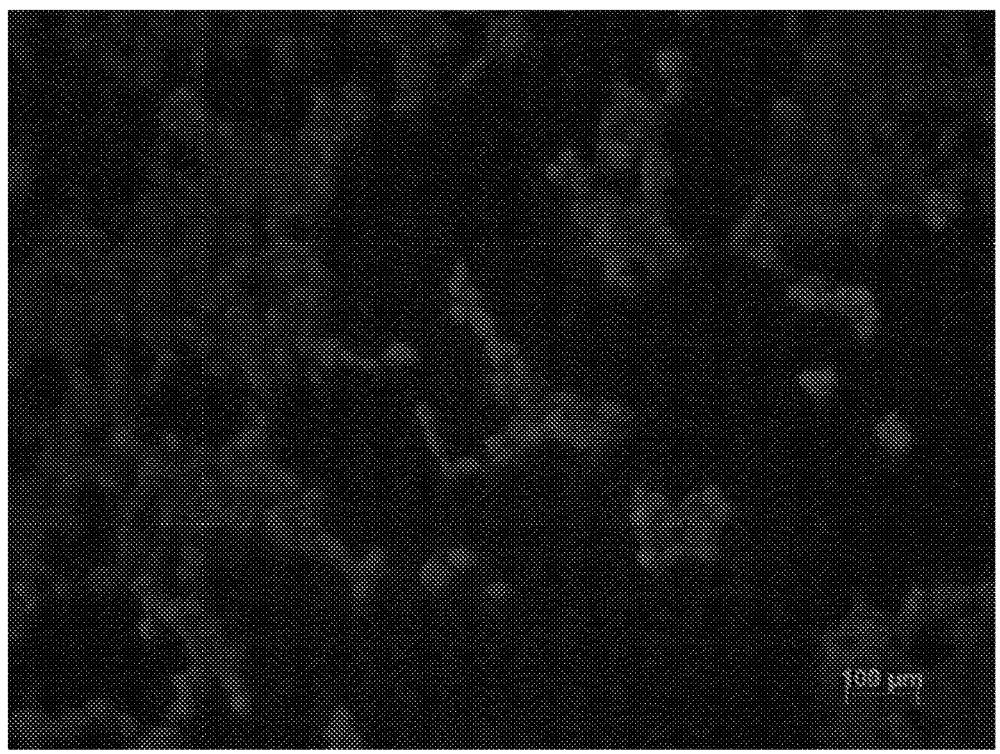

The expression of Bin1 increases during AD and Bin1 mediates AD risk by modulating Tau. HEK293 T-REx™ cells expressing Tau were treated with anti-Bin1 antibody. Tau was probed for using different antibodies to determine the expression of total Tau and phosphorylated Tau. Notably, both total tau and phosphorylated tau are increased in AD (Sjögren et al. (2001) J. Neurol. Neurosurg. Psychiatry 70:624-630). The expression of total Tau was found to decrease in Bin1 treated Tau expressing HEK cells when probed with DA9 and Tau 5 antibodies. The level of phosphorylated Tau was also decreased after treatment with anti-Bin1 antibodies as determined by probing with PHF1 antibody (FIG. 8). To confirm that anti-Bin1 antibodies reduced the expression of Tau, Tau expression was monitored using fluorescence microscopy. The intensity of fluorescence was found to be less in HEK 293 T-REx™ cells treated with anti-Bin1 antibodies compared with untreated cells, which exhibited bright red fluorescence (FIG. 9). These studies demonstrate that anti-Bin1 antibodies can be used to reduce the expression of Tau and prevent/treat tauopathies such as AD.

Figure 10A:
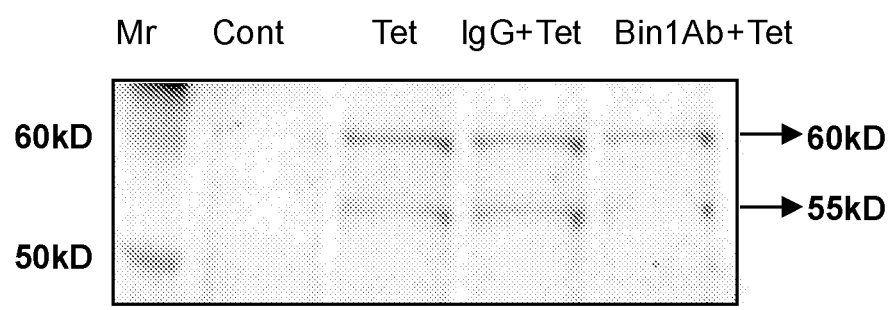
FIGS. 10A and 10B show that sera from a healthy donor and a patient with AD probed for the expression of tau in HEK 293 T-REx™ cells. Using sera from healthy donor (FIG. 10A) and patient with AD (FIG. 10B), the expression of tau in HEK 293 T-REx™ cells was studied. Anti-Bin1 antibodies treated HEK cells had low levels of tau oligomers when probed with healthy or diseased sera.
Figure 10B:
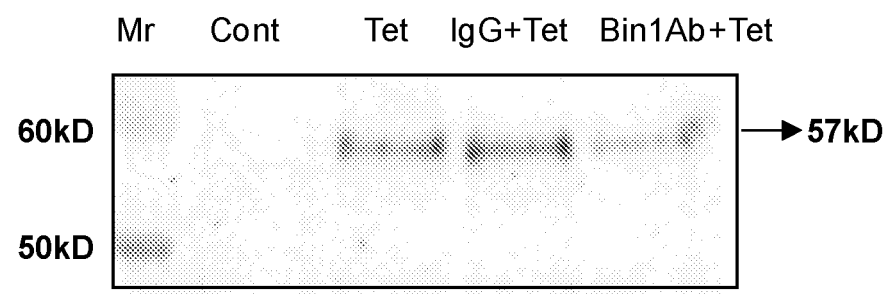

It is known that aging increases the incidence of AD. However, it is not known when the toxic forms of tau oligomers are formed in the brain. Using sera from a healthy donor (mid-forties) and a patient with AD, the expression of tau in HEK 293 T-REx™ cells was detected. Anti-Bin1 antibody treated HEK cells had low levels of tau oligomers when probed with healthy or diseased sera (FIG. 10). The study further demonstrates that anti-Bin1 antibodies reduce the expression of Tau.

Figure 11:
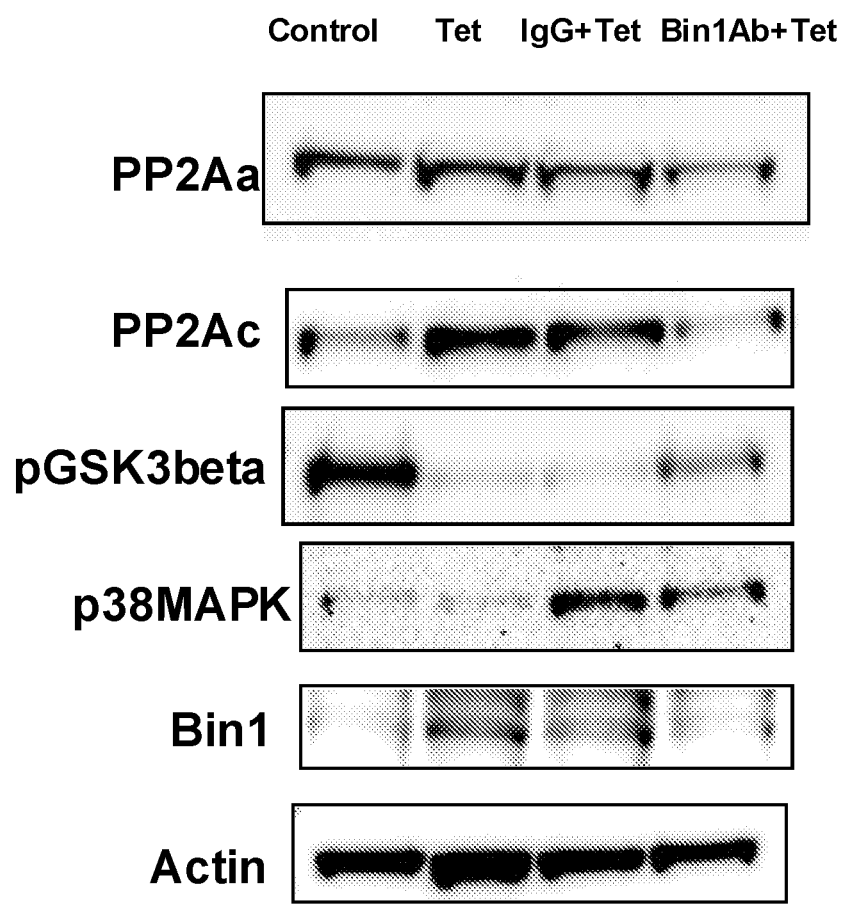
FIG. 11 shows that anti-Bin1 antibody treatment of Tau alters cell signaling proteins. Anti-Bin1 antibody treated HEK 293 T-REx™ cells expressing tau had altered expression of PP2A subunit a, PP2A subunit c, pGSK3beta, p38MAPK and also low expression of Bin1 as determined by western blotting.

Western blotting experiments using the anti-Bin1 antibody 2F11 demonstrated that the Bin1 protein is increased in the presence of Tau, whereas the expression is decreased on treatment with the anti-Bin1 antibody 99D. Tau phosphorylation is regulated by a balance between tau kinase and phosphatase activities. Disruption of this equilibrium may be at the origin of abnormal tau phosphorylation and thereby contribute to tau aggregation (Martin et al. (2013) Ageing Res. Rev., 12:39-49). Protein phosphatase 2A (PP2A) is a large family of enzymes that account for the majority of brain Ser/Thr phosphatase activity. PP2A consists of a dimeric core enzyme composed of the structural A and catalytic C subunits, and a regulatory B subunit. Here, it was determined that anti-Bin1 antibodies lower the expression of PP2A subunit c. The anti-Bin1 antibody also decreases the expression of p38MAPK compared to IgG treated HEK cells (FIG. 11).

Lastly, in transgenic mice overexpressing tau protein, injection of lithium increases phosphorylation of GSK3β (Muyllaert et al. (2008) Genes Brain Behav., 7:57-66). Here, the treatment with anti-Bin1 antibody increased phosphorylation of GSK3β compared to untreated controls (FIG. 11).

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating, inhibiting, and/or preventing an inflammatory bowel disease in a subject in need thereof, said method comprising administering at least one anti-bridging integrator 1 (Bin1) antibody or fragment thereof to said subject, wherein said anti-Bin1 antibody or fragment thereof is immunologically specific for the Myc-binding domain of Bin1, wherein said anti-Bin1 antibody is monoclonal antibody 99D or an antigen-binding fragment of monoclonal antibody 99D.

2. The method of claim 1, comprising administering a composition comprising at least one anti-Bin1 antibody or fragment thereof and at least one pharmaceutically acceptable carrier.

3. The method of claim 1, wherein said anti-Bin1 antibody or fragment thereof is immunologically specific for SEQ ID NO: 2.

4. The method of claim 1, wherein said inflammatory bowel disease is ulcerative colitis or Crohn's disease.

5. The method of claim 1, wherein said method further comprises the administration of at least one anti-inflammatory.

6. The method of claim 1 for treating an inflammatory bowel disease in a subject in need thereof.

* * * * *